United States Patent [19]

Bugaut et al.

[11] Patent Number: 4,466,806
[45] Date of Patent: Aug. 21, 1984

[54] DYEING COMPOSITIONS CONTAINING 3-AMINO-4-NITROANISOLE DERIVATIVES AND THEIR USE IN DYEING KERATIN FIBRES AS WELL AS CERTAIN NEW SAID DERIVATIVES

[75] Inventors: Andrée Bugaut, Boulogne-Billancourt; Patrick Andrillon, Chelles, both of France

[73] Assignee: L'Oreal, Paris, France

[21] Appl. No.: 291,099

[22] Filed: Aug. 7, 1981

[30] Foreign Application Priority Data

Aug. 8, 1980 [FR] France ................................ 80 17618

[51] Int. Cl.³ ............................................. A61K 7/13
[52] U.S. Cl. ......................................... 8/414; 8/406; 8/407
[58] Field of Search ......................... 8/406, 407, 414; 564/441

[56] References Cited

U.S. PATENT DOCUMENTS 3,642,423  2/1972  Bil et al. .................................. 8/414

FOREIGN PATENT DOCUMENTS 2549451  5/1976  Fed. Rep. of Germany .......... 8/414
2195424  3/1974  France .
2025958  7/1978  United Kingdom .
1531605  11/1978  United Kingdom .

OTHER PUBLICATIONS

Corbett, J. Soc. Dyers & Chem. (JSDC), vol. 83, pp. 273–276 (1967).

*Primary Examiner*—Albert T. Meyers
*Assistant Examiner*—John M. Kilcoyne
*Attorney, Agent, or Firm*—Fleit, Jacobson, Cohn & Price

[57] ABSTRACT

The invention provides compositions which comprise, in an aqueous, alcoholic or aqueous-alcoholic vehicle, at least one compound of the general formula:

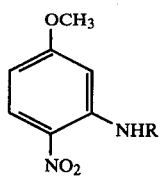

in which R denotes a monohydroxyalkyl radical containing from 2 to 6 carbon atoms or a polyhydroxyalkyl radical containing from 3 to 6 carbon atoms. These dyeing compositions make it possible to obtain, on the hair, yellow shades with a very high chromaticity and possessing very good fastness to light and to washing.

28 Claims, No Drawings

DYEING COMPOSITIONS CONTAINING 3-AMINO-4-NITROANISOLE DERIVATIVES AND THEIR USE IN DYEING KERATIN FIBRES AS WELL AS CERTAIN NEW SAID DERIVATIVES

The present invention relates to dyeing compositions which can be used in dyeing keratin fibres, and in particular human hair, and which comprise nitro dyestuffs of the 3-amino-4-nitroanisole type.

Nitro derivatives of the benzene series, having the formula:

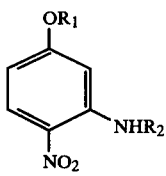

in which $R_1$ denotes a methyl, ethyl or propyl radical and $R_2$ denotes hydrogen or a methyl radical, are known.

However, the tinctorial strengths of the compounds having the above formula are too low with respect to keratin fibres for them to be used in hair dyeing.

In the course of our researches, we have discovered that, amongst the nitro derivatives of the benzene series having a structure similar to that of the above compounds, and especially amongst the 3-amino-4-nitroanisole derivatives, some are, surprisingly, particularly valuable for dyeing keratin fibres. These are the compounds having the general formula:

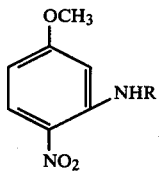

in which R denotes a lower monohydroxyalkyl radical containing from 2 to 6 carbon atoms or a lower polyhydroxyalkyl radical containing from 3 to 6 carbon atoms.

Preferred lower monohydroxyalkyl radicals which may be mentioned are the β-hydroxyethyl and β-hydroxypropyl radicals and the preferred lower polyhydroxyalkyl radical which may be mentioned is the β,γ-dihydroxypropyl radical.

In fact, when using compounds of the formula (I) according to the invention in dyeing compositions, it is possible to obtain yellow shades in which the chromaticity can reach a value as high as 8 to 10.

It will be recalled that the chromaticity is designated by the letter C in Munsell's notation, according to which a colour is defined by the formula:

HV/C in which the three parameters respectively denote the shade or "hue" (H), the intensity or "value" (V) and the purity or "chromaticity" (C), the sloping line simply being a convention.

In this connection, reference may be made to the publication "Official Digest", April 1964, pages 373 to 377.

Moreover, the nitro dyestuffs of the formula (I) above possess the very valuable property of being non-mutagenic.

The non-mutagenic character of these dyestuffs has been assessed by the Ames test on *Salmonella typhimurium*, with or without S9 mix, either not activated or activated by Arochlor (prior treatment of the rats with Arochlor); this has been carried out on the five strains TA 1535, TA 1537, TA 100, TA 1538 and TA 98.

As regards the Ames test, reference may be made to the following literature: B. N. AMES, H. O. KAMMEN and E. YAMASAKI, "Dyes are mutagenic; Identification of a variety of mutagenic ingredients", Proc. Nat. Acad. Sci. USA, Volume 72, No. 6, pages 2,423–2,427 (June 1975); and B. N. AMES, J. McCANN and E. YAMASAKI, "Methods for detecting carcinogens and mutagens with Salmonella mammalian microsome mutagenicity test", Mutation Res., 31 (1975), pages 347–364.

The nitro dyestuffs of the formula (I) exhibit the additional advantage of possessing very good fastness to light and to washing.

The present invention thus provides a dyeing composition for keratin fibres, and in particular for human hair, which comprises at least one compound of the formula (I) in an aqueous, alcoholic or aqueous-alcoholic vehicle, and also the use of the said dyeing compositions, especially in hair dyeing.

The present invention also provides the new compounds of the formula (I) in which R denotes the β-hydroxypropyl or β,γ-dihydroxypropyl radical.

The compounds of the formula (I) can be prepared by a two-stage process in accordance with the following reaction scheme:

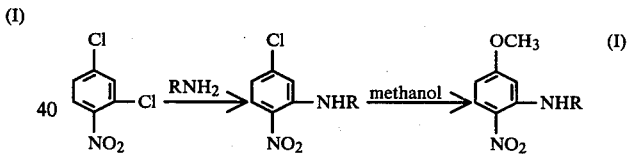

In a first stage, an aliphatic amine $RNH_2$, in which R denotes a lower monohydroxyalkyl or lower polyhydroxyalkyl radical, is condensed with 2,4-dichloronitrobenzene under sufficiently mild conditions for the substitution of the chlorine atom in the ortho-position to the nitro group, by the radical —NHR, to be selective.

In a second stage, methanol is condensed, in the presence of sodium hydroxide, with the 3-amino-4-nitrochlorobenzene derivative obtained in the first stage, in order to obtain the compound of the formula (I), which can be isolated and, if appropriate, recrystallised.

The present invention also provides a process for the preparation of the compounds of the formula (I) in which R denotes the β-hydroxypropyl or β,γ-dihydroxypropyl radical.

The compound of the formula (I) in which R denotes the β-hydroxyethyl radical, namely 3-N-(β-hydroxyethyl)-amino-4-nitroanisole, which is a known compound, can be prepared according to the invention by condensing methanol, in the presence of sodium hydroxide, with 3-N-(β-hydroxyethyl)-amino-4-nitrochlorobenzene, which is itself a known compound.

The concentration of the compounds of the formula (I) in the dyeing compositions according to the invention is suitably 0.001 to 5% by weight and preferably 0.01 to 3% by weight, relative to the total weight of the dyeing composition.

The pH of the dyeing compositions according to the invention is suitably 3 to 11.5 and preferably 5 to 11.5. It can be adjusted to the desired value with the aid of an alkalising agent such as ammonia, sodium carbonate, potassium carbonate or ammonium carbonate, sodium hydroxide or potassium hydroxide, alkanolamines such as mono-, di- or tri-ethanolamine, or alkylamines such as ethylamine or triethylamine, or with the aid of an acidifying agent such as phosphoric, hydrochloric, tartaric, acetic, lactic or citric acid.

The compositions according to the invention can also contain other direct dyestuffs such as azo or anthraquinone dyestuffs, nitro benzene dyestuffs indoanilines, indophenols, indamines, or hydroxynaphthoquinones such as juglone (5-hydroxy-1,4-naphthoquinone) or lawsone (2-hydroxy-1,4-naphthoquinone).

The concentrations of these direct dyestuffs other than the dyestuffs of the formula (I) is conveniently 0.001 to 5% by weight, relative to the total weight of the composition.

The dyeing compositions according to the invention can also contain anionic, cationic, non-ionic or amphoteric surface-active agents or mixtures thereof.

The surface-active products are generally present in the compositions according to the invention in an amount from 0.5 to 55% by weight and preferably 4 to 40% by weight, relative to the total weight of the composition.

Organic solvents can also be included in the compositions according to the invention, in order to solubilise compounds which would not be sufficiently soluble in water. Amongst the solvents which can advantageously be used, there may be mentioned lower alkanols such as ethanol and isopropanol, glycerol, glycols or glycol ethers, such as 2-butoxyethanol, ethylene glycol, ethylene glycol monoethyl ether, propylene glycol, and diethylene glycol monoethyl ether and monomethyl ether, and also analogous products and mixtures thereof. These solvents are preferably present in proportions from 1 to 75% by weight and more particularly from 5 to 50% by weight, relative to the total weight of the composition.

The compositions according to the invention can be thickened, preferably with sodium alginate, gum arabic, cellulose derivatives such as methylcellulose, hydroxyethylcellulose, hydroxypropylmethylcellulose and carboxymethylcellulose, and various polymers acting as thickeners, in particular acrylic acid derivatives. It is also possible to use inorganic thickeners such as bentonite. These thickeners are preferably present in proportions from 0.5 to 10% by weight and in particular 0.5 to 3% by weight, relative to the total weight of the composition.

The compositions according to the invention can also contain various adjuvants normally used in hair-dyeing compositions, and in particular penetrating agents, sequestering agents, film-forming agents, buffers and perfumes.

The dyeing compositions according to the invention can be presented in various forms such as liquids, creams or gels, or in any other form suitable for dyeing hair. They can also be packaged in aerosol flasks, in the presence of a propellant.

The compositions according to the invention, containing at least one compound of the formula (I), can be used in a process for dyeing hair by direct colouration.

These compositions are applied to the hair for, say, 5 to 40 minutes, this application being followed by rinsing, washing, if appropriate, and drying the hair.

The compositions according to the invention can also be used in the form of hair wavesetting lotions which are intended to impart both a slight colouration to the hair and to improve the hold of the set.

In this case, they can be presented in the form of aqueous-alcoholic solutions containing at least one cosmetic resin, and can be applied to damp hair which has been washed and rinsed beforehand; the hair is then wound onto rollers and dried.

The cosmetic resins used in the wavesetting lotions can be, in particular, polyvinylpyrrolidone and copolymers of crotonic acid/vinyl acetate, vinylpyrrolidone/vinyl acetate, maleic anhydride/butyl vinyl ether and maleic anhydride/methyl vinyl ether. These cosmetic resins are suitably used in the compositions of the invention in an amount of 1 to 3% by weight and preferably 1 to 2% by weight, based on the total weight of the composition.

The compounds of the formula (I) can also be used in oxidation dyeing compositions in accordance with a hair-dyeing process which involves development by means of an oxidising agent.

In this case, the compositions according to the invention contain, in association with at least one nitro dyestuff of the formula (I), one or more oxidation dyestuff precursors of the ortho or para type or a mixture thereof.

They can contain, for example, para-phenylene diamines such as: para-phenylenediamine, para-toluylenediamine, 2,6-dimethyl-para-phenylenediamine, 2,6-dimethyl-3-methoxy-para-phenylenediamine, N-($\beta$-methoxyethyl)-para-phenylenediamine, 4-N-[$\beta$-($\beta$'-hydroxyethoxy)-ethyl]-aminoaniline, 4-N,N-di-($\beta$-hydroxyethyl)-aminoaniline and 4-N-ethyl-N-carbamylmethyl-aminoaniline and also their salts.

They can also contain para-aminophenols, for example: para-aminophenol, N-methyl-para-aminophenol, 2-chloro-4-aminophenol, 3-chloro-4-aminophenol and 2-methyl-4-aminophenol and their salts.

They can also contain heterocyclic derivatives, for example: 2,5-diaminopyridine and 7-aminobenzomorpholine.

Amongst the dyestuff precursors of the ortho type, there may be mentioned ortho-phenylenediamines, ortho-aminophenols and pyrocatechols, optionally containing substituents on the nucleus or on one of the amine groups.

The compositions according to the invention can contain, in association with the dyestuff precursors of the ortho or para type, couplers which are well known in the state of the art.

Couplers which may be mentioned in particular are: meta-diphenols such as: resorcinol, 2-methylresorcinol and 5-methylresorcinol; meta-aminophenols such as: meta-aminophenol, 2-methyl-5-aminophenol, 2-methyl-5-N-($\beta$-hydroxyethyl)-aminophenol, 2-methyl-5-N-($\beta$-mesylaminoethyl)-aminophenol, 2,6-dimethyl-3-aminophenol and 6-hydroxybenzomorpholine and their salts; meta-phenylenediamines such as: 2,4-diaminoanisole, 2,4-diaminophenoxyethanol, 6-aminobenzomorpholine and 2-N-($\beta$-hydroxyethyl)-amino-4-aminophenoxyethanol and their salts; and meta-acylaminophenols, meta-ureidophenols and meta-carbalkoxyaminophenols such as: 2-methyl-5-acetylaminophenol, 2,6-dimethyl-5- acetylaminophenol, 2-methyl-5-ureidophenol and 2-methyl-5-carbethoxyaminophenol.

Finally, the following may be mentioned as other couplers which can be used in the compositions of the invention: α-naphthol, couplers possessing an active methylene group, such as diketone compounds and pyrazolones, and heterocyclic couplers such as 2,4-diaminopyridine, and also their salts.

Other oxidation dyestuff precursors which can be present in the compositions of the invention include leuco derivatives of indoanilines, of indamines and/or of indophenols, for example: 4,4'-dihydroxy-2-amino-5-methyldiphenylamine, 2-amino-4-hydroxy-5-methyl-4'-N,N-(β-hydroxyethyl)-aminodiphenylamine and 2,4-dihydroxy-5-methyl-4'-N-(β-methoxyethyl)-aminodiphenylamine dihydrochloride.

Other hair colouration precursors which can be present include precursors of the benzene series containing at least three hydroxy, methoxy, and/or amino substituents on the nucleus, such as: 2,6-diaminohydroquinone dihydrochloride, 2,6-diamino-4-N,N-diethylaminophenol trihydrochloride, 2,4-diaminophenol dihydrochloride, 1,2,4-trihydroxybenzene, 2,3,5-trihydroxytoluene or 4-methoxy-2-amino-N-(β-hydroxyethyl)-aniline.

Preferably, antioxidants such as sodium sulphite, thioglycolic acid, sodium bisulphite, ascorbic acid and hydroquinone are added to the compositions according to the invention which comprise oxidation dyestuff precursors. These antioxidants are advantageously present in proportions of 0.05 to 1.5% by weight, relative to the total weight of the composition.

The oxidation dyestuff precursors of the "para" or "ortho" type are suitably used in the compositions of the invention at a concentration of 0.001 to 5% by weight and preferably of 0.03 to 2%, based on the total weight of the composition. The couplers are suitably used at a concentration of 0.001 to 5% by weight and preferably of 0.015 to 2% by weight.

According to a first embodiment, the hair-dyeing process according to the invention, which employs development by means of an oxidising agent, consists in applying, to the hair, the dyeing composition comprising both the direct dyestuff and the dyestuff precursor, and in developing the colouration with the aid of an oxidising agent which is present in the dyeing composition or is applied to the hair in a second stage.

The oxidising agent is preferably hydrogen peroxide, urea peroxide or a per-salt. It is preferred to use a solution of hydrogen peroxide of 20 volumes strength.

According to another embodiment of the dyeing process according to the invention, which employs development by means of an oxidising agent, a solution containing at least one direct dyestuff of the formula (I), optionally in association with other direct dyestuffs, is mixed at the time of use with a solution containing at least one dyestuff precursor but not containing any direct dyestuff, and the colouration is developed with the aid of an oxidising agent, which is added to the mixture or is applied to the hair in a second stage.

Once the oxidising agent has been applied to the hair, it is left on the hair for, say, 10 to 40 minutes, preferably 15 to 30 minutes, after which the hair is rinsed, shampooed and rinsed again, if appropriate, and dried.

The present invention is further illustrated by the following Examples. Examples 1 to 3 illustrate the preparation of compounds of formula (I) for use in the compositions of this invention.

EXAMPLE 1

Preparation of 3-N-(β-hydroxyethyl)-amino-4-nitroanisole 0.0462 mol (10 g) of 3-N-(β-hydroxyethyl)-amino-4-nitrochlorobenzene [known product described by P Clarke in J C S 4,763, 7 (1963)] is dissolved in 100 ml of methanol in which 3.7 g of sodium hydroxide pellets have been dissolved beforehand. The solution is heated under reflux for 9 hours. After the reaction medium has been filtered hot, the filtrate is cooled to 0° C. The desired product crystallises. It is filtered off and recrystallised firstly from ethanol and secondly from benzene.

After drying in vacuo, the desired product melts at 108° C.

| Analysis | Calculated for $C_9H_{12}N_2O_4$ | Found |
|---|---|---|
| C % | 50.94 | 50.72 |
| H % | 5.70 | 5.64 |
| N % | 13.20 | 13.30 |
| O % | 30.16 | 30.11 |

When applied to bleached hair at 28° C. for 30 minutes, 3-N-(β-hydroxyethyl)-amino-4-nitroanisole, as a solution containing 0.059% (0.00028 mol) in a mixture of 15 ml of ethanol and 85 ml of water, adjusted to pH 9 with $NH_4OH$, gives a yellow colour which can be expressed according to Munsell's notation by the formula: 5 Y 8.25/10. It is thus found that 3-N-(β-hydroxyethyl)-amino-4-nitroanisole makes it possible to obtain a yellow shade with a high chromaticity equal to 10.

EXAMPLE 2

Preparation of 3-N-(β-hydroxypropyl)-amino-4-nitroanisole

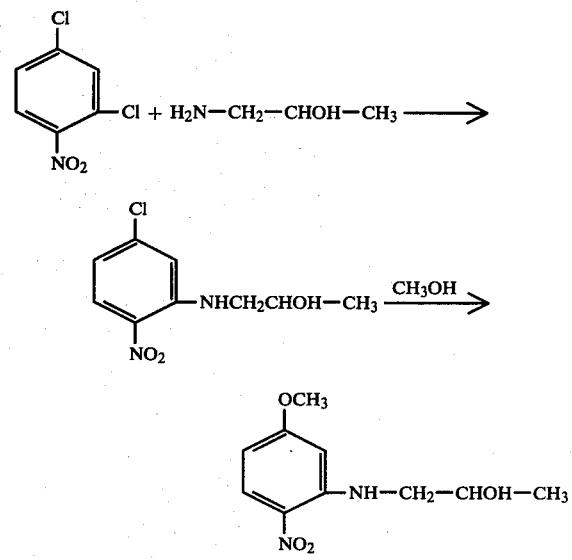

1st step

Preparation of 3-N-(β-hydroxypropyl)-amino-4-nitrochlorobenzene 0.208 mol (40 g) of 2,4-dichlorobenzene is added gradually, whilst stirring, to 80 ml of 1-aminopropan-2-ol heated to 80° C. beforehand, in such a way that the temperature does not exceed 85° C. When the addition has ended, the reaction medium is kept at about 85° C. for 1 hour 30 minutes and is then poured into 250 ml of ice-cooled normal hydrochloric acid. The desired product precipitates. It is filtered off, washed with water and recrystallised twice from ethanol.

After drying in vacuo, it melts at 110° C.

| Analysis | Calculated for $C_9H_{11}ClN_2O_3$ | Found |
|---|---|---|
| C % | 46.86 | 46.71 |
| H % | 4.81 | 4.79 |
| N % | 12.15 | 12.09 |
| O % | 20.81 | 20.90 |
| Cl % | 15.37 | 15.45 |

2nd step

Preparation of 3-N-(β-hydroxypropyl)-amino-4-nitroanisole 0.06 mol (13.8 g) of 3-N-(β-hydroxypropyl)-amino-4-nitrochlorobenzene is dissolved in 140 ml of methanol in which 7.2 g of sodium hydroxide pellets have been dissolved beforehand.

The solution is heated under reflux for 9 hours. After the hot reaction medium has been filtered, the desired product crystallises on cooling. It is filtered off and then recrystallised from benzene. After drying in vacuo, it melts at 108° C.

| Analysis | Calculated for $C_{10}H_{14}N_2O_4$ | Found |
|---|---|---|
| C % | 53.09 | 53.22 |
| H % | 6.24 | 6.31 |
| N % | 12.38 | 12.37 |
| O % | 28.29 | 28.41 |

When applied to bleached hair at 28° C. for 30 minutes, a solution containing 0.063% of 3-N-(β-hydroxypropyl)-amino-4-nitroanisole (0.00028 mol) in a mixture of 15 ml of ethanol and 85 ml of water, adjusted to pH 9 by adding NH₄OH, makes it possible to obtain a yellow colouration which can be written as follows, according to Munsell's notation: 4.5 Y 8.5/8.5.

3-N-(β-hydroxypropyl)-amino-4-nitroanisole thus also gives a colouration with a high chromaticity, which is equal to 8.5.

EXAMPLE 3

3-N-(β,γ-dihydroxypropyl)-amino-4-nitroanisole

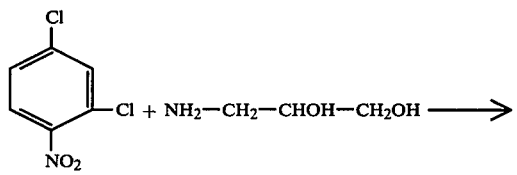

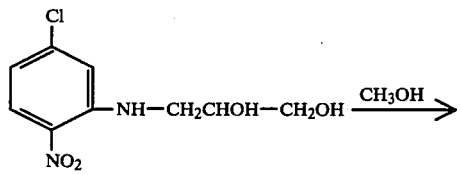

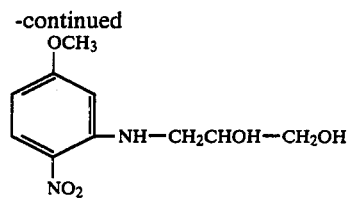

1st step

Preparation of 3-N-(β,γ-dihydroxypropyl)-amino-4-nitrochlorobenzene 19.2 g (0.1 mol) of 2,4-dichloronitrobenzene are dissolved in 15 ml of dioxane. This solution is added gradually, whilst stirring, to a mixture consisting of 0.15 mol (13.7 g) of 3-aminopropane-1,2-diol in 25 ml of dioxane containing 5.8 g of sodium carbonate in suspension. The addition is carried out whilst keeping the temperature of the reaction medium at about 80° C. When the addition has ended, the reaction medium is kept at 80° C. for 4 hours and then poured into 150 ml of ice-cooled water. The mixture is neutralised with hydrochloric acid. The desired product crystallises. It is filtered off, washed with water and then recrystallised from ethanol. After drying in vacuo, it melts at 160° C.

| Analysis | Calculated for $C_9H_{11}ClN_2O_4$ | Found |
|---|---|---|
| C % | 43.82 | 43.81 |
| H % | 4.50 | 4.45 |
| N % | 11.36 | 11.42 |
| O % | 25.95 | 25.82 |
| Cl % | 14.37 | 14.49 |

2nd step

Preparation of 3-N-(β,γ-dihydroxypropyl)-amino-4-nitroanisole 3.2 g of sodium hydroxide pellets are dissolved in 70 ml of methanol, and 0.03 mol (7.4 g) of 3-N-(β,γ-dihydroxypropyl)-amino-4-nitrochlorobenzene is then added. The mixture is heated under reflux for 6 hours 30 minutes. After the hot reaction medium has been filtered, the desired product crystallises on cooling. It is filtered off, washed with water and recrystallised from ethanol. After drying in vacuo, it melts at 130° C.

| Analysis | Calculated for $C_{10}H_{14}N_2O_5$ | Found |
|---|---|---|
| C % | 49.58 | 49.70 |
| H % | 5.83 | 5.85 |
| N % | 11.57 | 11.51 |
| O % | 33.03 | 32.86 |

When applied to bleached hair at 28° C. for 30 minutes, a solution of 3-N-(β,γ-dihydroxypropyl)-amino-4-nitroanisole containing 0.068% (0.00028 mol) of the latter in a mixture of 15 ml of ethanol and 85 ml of water, adjusted to pH 9 with NH₄OH, gives a yellow colouration which is expressed according to Munsell's notation by the formula: 5 Y 8.5/9.5.

It is consequently found that 3-N-(β,γ-dihydroxypropyl)-amino-4-nitroanisole gives a yellow colouration with a high chromaticity equal to 9.5.

EXAMPLE 4

Direct dyeing

The following dyeing composition is prepared:

| | |
|---|---|
| 3-N—(β,γ-Dihydroxypropyl)-amino-4-nitroanisole | 0.13 g |
| 3-Nitro-4-aminophenol | 0.257 g |
| Tetraaminoanthraquinone | 0.4 g |
| 2-Butoxyethanol | 10 g |
| Alfol C$_{16}$/C$_{18}$ E | 8 g |
| Lanette wax E | 0.5 g |
| Cemulsol B | 1 g |
| Oleyl diethanolamide | 1.5 g |
| Triethanolamine | 1 g |
| Water q.s.p. | 100 g |

This composition has a pH of 8.

When applied for 35 minutes at 30° C. to hair which has been bleached white beforehand, this mixture imparts to the hair, after rinsing and shampooing, a copper colouration.

EXAMPLE 5

Direct dyeing

The following dyeing composition is prepared:

| | |
|---|---|
| 3-N—(β,γ-Dihydroxypropyl)-amino-4-nitroanisole | 0.4 g |
| 3-Nitro-4-N'—methylamino-N—β-aminoethylaniline dihydrobromide | 0.1 g |
| Juglone | 0.6 g |
| Carboxymethylcellulose | 2 g |
| 96° strength alcohol | 5 g |
| Triethanolamine | 1 g |
| Water q.s.p. | 100 g |

The above composition has a pH of 7.8.

When applied for 30 minutes at 28° C. to hair which has been bleached straw yellow beforehand, this mixture imparts to the hair, after rinsing and shampooing, a coppery medium chestnut colouration.

EXAMPLE 6

Wavesetting lotion

The following wavesetting lotion is prepared:

| | |
|---|---|
| 3-N—(β,γ-Dihydroxypropyl)-amino-4-nitroanisole | 0.04 g |
| 2-N—(4'-Methylamino-3'-chlorophenyl)-methyl-5-ureidobenzoquinone-imine | 0.074 g |
| 2-N—(4'-Ethyl-carbamylmethyl-aminophenyl)-methyl-5-ureidobenzoquinone-imine | 0.06 g |
| Copolymer { vinyl acetate 90% / crotonic acid 10% } | 2 g |
| 96° strength alcohol | 50 g |
| 20% strength by weight ethanolamine | 3 g |
| Water q.s.p. | 100 g |

This lotion has a pH of 7.

When applied as a wavesetting lotion to hair which has been bleached white beforehand, this mixture imparts to the hair a grey-beige colouration with a mauve sheen.

EXAMPLE 7

Wavesetting lotion

The following wavesetting lotion is prepared:

| | |
|---|---|
| 3-N—(β-Hydroxyethyl)-amino-4-nitroanisole | 0.10 g |
| 2-N—(4'-Methylamino-3'-chlorophenyl)-methyl-5-ureidobenzoquinone-imine | 0.05 g |
| Copolymer { vinylpyrrolidone 30% / vinyl acetate 70% } | 2 g |
| E 335 sold by General Aniline and Film Corporation | |
| Ethanol | 40 g |
| 20% strength by weight triethanolamine | 2 g |
| Water q.s.p. | 100 g |

This lotion has a pH of 7.2.

When applied as a wavesetting lotion to hair which has been bleached white, this composition imparts a golden sandy colouration to the hair.

EXAMPLE 8

Direct dyeing

The following dyeing composition is prepared:

| | |
|---|---|
| 3-N—(β-Hydroxypropyl)-amino-4-nitroanisole | 0.25 g |
| 2-Amino-3-nitrophenol | 0.05 g |
| 3-Nitro-4-N'—methylamino-N—β-aminoethylaniline dihydrobromide | 0.1 g |
| 2-N—(β-Hydroxyethyl)-amino-5-[4'-(di-β-hydroxyethyl)-amino]-anilino-1,4-benzoquinone | 0.08 g |
| 96° strength alcohol | 10 g |
| Diethanolamides of copra fatty acids | 2.2 g |
| Lauric acid | 0.8 g |
| Ethylene glycol monoethyl ether | 2 g |
| Monoethanolamine | 1.1 g |
| Water q.s.p. | 100 g |

This composition has a pH of 10.2.

When applied for 25 minutes at 30° C. to hair which has been bleached white beforehand, this mixture imparts to the hair, after rinsing and shampooing, a light mahogany colouration.

EXAMPLE 9

Direct dyeing

The following dyeing mixture is prepared:

| | |
|---|---|
| 3-N—(β-Hydroxypropyl)-amino-4-nitroanisole | 0.26 g |
| 2-N—(β-Hydroxyethyl)-amino-5-[4'-(di-β-hydroxyethyl)-amino]-anilino-1,4-benzoquinone | 0.20 g |
| 3-Nitro-4-N—(β-hydroxyethyl)-amino-6-chloroaniline | 0.09 g |
| 96° strength alcohol | 10 g |
| Tween 80 | 12 g |
| Oleic acid | 20 g |
| Monoethanolamine | 2 g |
| Water q.s.p. | 100 g |

The above mixture has a pH of 7.

When applied to bleached hair for 30 minutes at 30° C., this mixture imparts to the hair, after rinsing and shampooing, a golden blond colouration.

EXAMPLE 10

Direct dyeing

The following dyeing composition is prepared:

| | |
|---|---|
| 3-N—(β,γ-Dihydroxypropyl)-amino-4-nitroanisole | 0.011 g |
| 3-Nitro-4-N'—methylamino-N—β-aminoethylaniline dihydrobromide | 0.02 g |
| 2-Butoxyethanol | 10 g |
| Carboxymethylcellulose | 10 g |
| Monoethanolamine | 10 g |
| Water q.s.p. | 100 g |

The above composition has a pH of 11.5.

When applied to bleached hair for 35 minutes at 28° C., this mixture imparts to the hair, after rinsing and shampooing, a pink champagne colouration.

EXAMPLE 11

Oxidation dyeing

The following dyeing composition is prepared:

| | |
|---|---|
| 3-N—(β,γ-Dihydroxypropyl)-amino-4-nitroanisole | 0.052 g |
| Para-phenylenediamine | 0.05 g |
| Resorcinol | 0.052 g |
| Meta-aminophenol | 0.021 g |
| 2-Methyl-5-N—(β-hydroxyethyl)-aminophenol | 0.022 g |
| Para-aminophenol | 0.018 g |
| 2-Amino-3-nitrophenol | 0.028 g |
| Cemulsol NP4 | 12 g |
| Cemulsol NP9 | 15 g |
| Oleyl alcohol oxyethylenated with 2 mols of ethylene oxide (per mole of alcohol) | 1.5 g |
| Oleyl alcohol oxyethylenated with 4 mols of ethylene oxide | 1.5 g |
| Propylene glycol | 6 g |
| Trilon B | 0.12 g |
| Thioglycolic acid | 0.6 g |
| 22° B. strength ammonia solution | 11 g |
| Water q.s.p. | 100 g |

This composition has a pH of 10.6.

80 g of hydrogen peroxide of 20 volumes strength are added at the time of application.

When applied for 30 minutes at 30° C. to hair which has been bleached straw yellow beforehand, this mixture imparts to the hair, after rinsing and shampooing, a golden light chestnut colouration.

EXAMPLE 12

Oxidation dyeing

The following dyeing composition is prepared:

| | |
|---|---|
| 3-N—(β-Hydroxypropyl)-amino-4-nitroanisole | 0.51 g |
| 2-Methylresorcinol | 0.64 g |
| Meta-aminophenol | 0.207 g |
| 2,4-Diaminophenoxyethanol dihydrochloride | 0.05 g |
| Para-aminophenol | 0.3 g |
| N—Methyl-para-aminophenol sulphate | 0.203 g |
| Para-phenylenediamine | 0.155 g |
| Carbopol 934 | 1.5 g |
| 96° strength alcohol | 11 g |
| 2-Butoxyethanol | 5 g |
| Trimethylcetylammonium bromide | 1 g |
| Trilon B | 0.1 g |
| Thioglycolic acid | 0.2 g |
| 22° B. strength ammonia solution | 10 g |
| Water q.s.p. | 100 g |

This composition has a pH of 10.4.

100 g of hydrogen peroxide of 20 volumes strength are added at the time of application. When applied for 30 minutes at 30° C. to hair which has been bleached straw yellow beforehand, this mixture imparts to the hair, after rinsing and shampooing, a chestnut colouration.

EXAMPLE 13

Oxidation dyeing

The following dyeing composition (A) is prepared:

| | |
|---|---|
| 3-N—(β,γ-Dihydroxypropyl)-amino-4-nitroanisole | 0.155 g |
| 3-Nitro-4-N—(β-hydroxyethyl)-amino-6-chloroaniline | 0.1 g |
| 2-Methyl-5-amino-6-nitrophenol | 0.2 g |
| 2-Butoxyethanol | 10 g |

The following dyeing composition (B) is prepared:

| | |
|---|---|
| Para-phenylenediamine | 0.2 g |
| Para-aminophenol | 0.3 g |
| Resorcinol | 0.4 g |
| Meta-aminophenol | 0.1 g |
| 2-Methyl-5-N—(β-hydroxyethyl)-aminophenol | 0.215 g |
| Remcopal 334 | 21 g |
| Remcopal 349 | 24 g |
| Oleic acid | 4 g |
| 2-Butoxyethanol | 3 g |
| 96° strength ethanol | 10 g |
| Masquol DTPA | 2.5 g |
| 35° B. strength sodium bisulphite solution | 1 g |
| 22° B. strength ammonia solution | 10 g |
| Water q.s.p. | 100 g |

Solution (A) and solution (B) are mixed at the time of use and 120 g of hydrogen peroxide of 20 volumes strength are then added to this mixture of pH 10.4.

When applied to 90% naturally white hair for 30 minutes at 28° C., this mixture imparts to the hair, after rinsing and shampooing, a light brown colouration.

The compositions of the various tradenames and Registered Trade Marks are given below.

| | |
|---|---|
| Alfol C16/C18E (50/50) | Cetyl/stearyl alcohol sold by Condea. |
| Lanette wax E | Partially sulphated cetyl/stearyl alcohol sold by Henkel. |
| Cemulsol B | Oxyethyleneated castor oil sold by Rhône Poulenc. |
| Tween 80 | Polyoxyethyleneated sorbitol monooleate. |
| Cemulsol NP4 | Nonylphenol oxyethylenated with 4 mols of ethylene oxide, sold by Rhône Poulenc. |
| Cemulsol NP9 | Nonylphenol oxyethylenated with 9 mols of ethylene oxide, sold by Rhône Poulenc. |
| Trilon B | Sodium salt of ethylenediaminetetraacetic acid. |
| Carbopol 934 | Acrylic acid polymer of molecular weight 2 to 3 million, sold by Goodrich Chemical Company. |
| Remcopal 334 | Nonylphenol oxyethylenated with 4 mols of ethylene oxide, sold by Gerland. |
| Remcopal 349 | Nonylphenol oxyethylenated with 9 mols of ethylene oxide, sold by Gerland. |
| Masquol DPTA | Sodium salt of diethylenetriaminepentaacetic acid. |

We claim:

1. A composition suitable for dyeing human hair which comprises an aqueous, alcoholic or aqueous-alcoholic vehicle and 0.001 to 5% by weight, relative to the total weight of the composition, of at least one compound of the general formula:

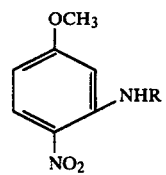

in which R denotes a monohydroxyalkyl radical containing from 2 to 6 carbon atoms or a polyhydroxyalkyl radical containing from 3 to 6 carbon atoms.

2. A composition according to claim 1 in which the compound of formula (I) comprises at least one of 3-N-(β-hydroxyethyl)-amino-4-nitroanisole, 3-N-(β-hydroxypropyl)-amino-4-nitroanisole and 3-N-(β,γ-dihydroxypropyl)-amino-4-nitroanisole.

3. A composition according to claim 1 which contains 0.01 to 3% by weight of at least one compound of formula (I) relative to the total weight of the composition.

4. A composition according to claim 1 which comprises one or more additional direct dyestuffs which are azo or anthraquinone dyestuffs, nitrobenzene dyestuffs, indoanilines, indophenols, indamines or hydroxynaphthoquinones, at a concentration of 0.001 to 5% by weight, based on the total weight of the composition.

5. A composition according to claim 1 which has a pH of 3 to 11.5.

6. A composition according to claim 5 which has a pH of 5 to 11.5.

7. A composition according to claim 1 which contains a surface-active agent, at a concentration of 0.5 to 55% by weight relative to the total weight of the composition.

8. A composition according to claim 7 which contains said surface-active agent at a concentration of 4 to 40% by weight, relative to the total weight of the composition.

9. A composition according to claim 1 which contains an organic solvent at a concentration of 1 to 75% by weight relative to the total weight of the composition.

10. A composition according to claim 9 which contains said organic solvent at a concentration of 5 to 50% by weight, relative to the total weight of the composition.

11. The composition according to claim 10 wherein the compound of formula (I) is 3-N-(β,γ-Dihydroxypropyl)-amino-4-nitroanisole.

12. A composition according to claim 1 which contains a thickener at a concentration of 0.5 to 10% by weight, relative to the total weight of the composition.

13. A composition according to claim 12 which contains said thickener at a concentration of 0.5 to 3% by weight, relative to the total weight of the composition.

14. A composition according to claim 1 which contains at least one cosmetic resin in an amount from 1 to 3% by weight based on the total weight of the composition.

15. A composition according to claim 14 which contains said cosmetic resin in an amount from 1 to 2% by weight relative to the total weight of the composition.

16. A composition according to claim 1 which comprises at least one oxidation ortho or para dyestuff precursor or a mixture thereof, at concentrations of 0.001 to 5% by weight based on the total weight of the composition.

17. A composition according to claim 16 which contains the precursor at a concentration of 0.03 to 2% by weight relative to the total weight of the composition.

18. A composition according to claim 16 in which the precursor is a para-phenylenediamine, para-aminophenol, ortho-phenylenediamine, ortho-aminophenol, pyrocatechol, or a salt thereof or a heterocyclic derivative.

19. A composition according to claim 16 and further comprising a coupler which is a meta-diphenol, meta-aminophenol, meta-phenylenediamine, meta-acylaminophenol, meta-ureidophenol, meta-carbalkoxyaminophenol or α-naphthol, a heterocyclic coupler or a coupler possessing an active methylene group, or a salt thereof at a concentration of 0.001 to 5% by weight based on the total weight of the composition.

20. A composition according to claim 19 which contains said coupler at a concentration of 0.015 to 2% by weight, relative to the total weight of the composition.

21. A composition according to claim 16 which contains 0.05 to 1.5% by weight of antioxidant, relative to the total weight of the composition.

22. Process for the direct dyeing of human hair, which comprises applying thereto an effective amount of a composition as defined in claim 1, leaving it on the hair for 5 to 40 minutes and then rinsing, optionally washing and then drying the hair.

23. Process for the oxidation dyeing of human hair, which comprises mixing, at the time of use an effective amount of, a composition as defined in claim 1 with an effective amount of a dyeing composition containing at least one oxidation dyestuff precursor, but not containing any direct dyestuff, applying the mixture to the hair and allowing the colouration to develop with the aid of an oxidation agent, which is added to the mixture or which is applied to the hair after said mixture.

24. A process for dyeing human hair which comprises the steps of:
applying an effective amount of a composition as defined in claim 1 to the hair,
leaving it on the hair for 5 to 40 minutes and then,
rinsing or washing and drying the hair.

25. Process for treating human hair which comprises applying to the hair which has been washed and rinsed beforehand an effective amount of a dyeing composition as defined in claim 14 and then winding the hair onto rollers and drying it.

26. Process for the oxidation dyeing of human hair which comprises applying thereto an effective amount of a composition as defined in claim 16 and allowing the colouration to develop with an oxidising agent which is present in the said composition, or which is applied to the hair after the said composition.

27. Process according to claim 26 or 23 in which after the dyeing composition or the mixture of dyeing composition and oxidising agent have been applied to the hair, it is left on the hair for 10 to 40 minutes and the hair is rinsed, shampooed and then dried.

28. A process according to claim 27 in which the hair is rinsed again after being shampooed and before being dried.

* * * * *